(12) United States Patent
Tsuchida et al.

(10) Patent No.: US 10,294,497 B2
(45) Date of Patent: *May 21, 2019

(54) HIGHLY EFFICIENT ETHANOL-FERMENTATION YEAST

(71) Applicant: HONDA MOTOR CO., LTD., Tokyo (JP)

(72) Inventors: Yoshiki Tsuchida, Saitama (JP); Norihiko Tsukagoshi, Saitama (JP); Ikumi Kurihara, Saitama (JP); Akihiko Aoyagi, Saitama (JP)

(73) Assignee: HONDA MOTOR CO., LTD., Tokyo (JP)

( * ) Notice: Subject to any disclaimer, the term of this patent is extended or adjusted under 35 U.S.C. 154(b) by 91 days.

This patent is subject to a terminal disclaimer.

(21) Appl. No.: 15/532,826

(22) PCT Filed: Dec. 5, 2014

(86) PCT No.: PCT/JP2014/082329
§ 371 (c)(1),
(2) Date: Jun. 2, 2017

(87) PCT Pub. No.: WO2016/088272
PCT Pub. Date: Jun. 9, 2016

(65) Prior Publication Data
US 2018/0237803 A1    Aug. 23, 2018

(51) Int. Cl.
*C12P 7/06* (2006.01)
*C12R 1/84* (2006.01)
*C12N 15/09* (2006.01)
*C12N 15/10* (2006.01)
*C12R 1/645* (2006.01)

(52) U.S. Cl.
CPC .............. *C12P 7/06* (2013.01); *C12N 15/102* (2013.01); *C12R 1/645* (2013.01); *C12R 1/84* (2013.01); *C12N 15/09* (2013.01); *Y02E 50/17* (2013.01)

(58) Field of Classification Search
None
See application file for complete search history.

(56) References Cited

U.S. PATENT DOCUMENTS

2013/0189788 A1    7/2013    Zhang et al.

FOREIGN PATENT DOCUMENTS

| JP | 2011-024500 | 2/2011 |
| JP | 2011-167096 | 9/2011 |
| JP | 2011-193788 | 10/2011 |
| JP | 2012-170422 | 9/2012 |
| WO | 2011/065539 | 6/2011 |

OTHER PUBLICATIONS

Han Li-Li et al., "Breeding of Higher Ethanol Fermentation of Xylose Strain with Protoplast Fusion and Mutagenisis", Liquor Making, vol. 35, No. 2, Mar. 2008, pp. 38-41, Sinkiang, China, Listed in International Search Report, English abstract included, 4 pages.
T. Granstrom et al., "Chemostat study of xylitol production by Candida guilliermondii", Appl Microbiol Biotechnol (2001) 55, pp. 36-42, Mar. 7, 2000, listed in International Search Report, English text, 7 pages.
Paul A. Bicho et al., "Induction of Xylose Reductase and Xylitol Dehydrogenase Activities in Pachysolen tannophilus and Pichia stipitis on Mixed Sugars", Applied and Environmental Microbiology, Jan. 1988, vol. 54, No. 1, pp. 50-54, Ontario, Canada, Discussed in specification, English text, 5 pages.
Cesar Fonseca et al., "L-Arabinose metabolism in Candida arabinofermentans PYCC 5603T and Pichia guilliermondii PYCC 3012: influence of sugar and oxygen on product formation", Appl Microbiol Biotechnol (2007), vol. 75, pp. 303-310, Listed in International Search Report, English text, 8 pages.
Min Zhang et al., "Metabolic Engineering of a Pentose Metabolism Pathway in Ethanologenic Zymomonas mobilis", Science, Jan. 13, 1995, vol. 267, pp. 240-243, Discussed in specification, English text, 6 pages.
Olena P. Ishchuk et al., "Overexpression of pyruvate decarboxylase in the yeast *Hansenula polymorpha* results in increased ethanol yield in high-temperature fermentation of xylose", FEMS Yeast Res (2008), pp. 1164-1174, English text, 11 pages.
International Search Report, dated Mar. 17, 2015 (dated Mar. 17, 2015), 2 pages.
European Search Report dated Apr. 25, 2018, 6 pages.
Schirmer-Michel, et al. "Production of Ethanol from Soybean Hull Hydrolysate by Osmotolerant Candida Guilliermondii NRRL Y-2075", Science Direct, Biosource Technology 99 (2008), pp. 2898-2904, 7 pages.
Matsushika, et al. "Ethanol Production from Xylose in Engineered *Saccharomyces cerevisiae* Strains: Current State and Perspectives", Appl Microbiol. Biotechnol (2009) 84:37-53, 17 pages.

*Primary Examiner* — Paul J Holland
(74) *Attorney, Agent, or Firm* — Rankin, Hill & Clark LLP

(57) ABSTRACT

An object of the present invention is to obtain fermentative yeast having highly efficient ethanol production without introducing a foreign gene. A further object is to obtain a fermentative yeast that is resistant to proliferation inhibitors such as organic acids, which prevent the proliferation of the fermentative yeast. *Meyerozyma guilliermondii* that can produce ethanol effectively from pentose and hexose was isolated by breeding. Moreover, resistance was imparted to the fermentative yeast by introducing transaldolase and alcohol dehydrogenase genes derived from *Meyerozyma guilliermondii* into the fermentative yeast.

1 Claim, 4 Drawing Sheets

Specification includes a Sequence Listing.

HIGHLY EFFICIENT ETHANOL-FERMENTATION YEAST

TECHNICAL FIELD

The present invention relates to a yeast for fermenting a saccharified solution in bioethanol production using lignocellulosic biomass.

In particular, the present invention relates to a yeast capable of effectively producing ethanol from pentose (which may be, hereinafter, also referred to as C5) and hexose (which may be, hereinafter, also referred to as C6) in bioethanol production using lignocellulosic biomass.

BACKGROUND ART

Bioethanol is expected to be a renewable resource that is produced by biomass. Moreover, since carbon dioxide that is produced by combustion of bioethanol is carbon neutral, increased use of bioethanol is considered to suppress increase of carbon dioxide, which is a main cause of the global warming.

Bioethanol is obtained by fermenting biomass and distilling and purifying ethanol. It is necessary to produce much alcohol from saccharified solutions for increasing the yield of bioethanol. Since the yeasts generally used in the process of bioethanol production cannot convert pentose such as xylose and arabinose into alcohol, only hexose has been used as raw materials for fermentation.

Typical biomass is reported to contain 35-45% of cellulose, 25-40% of hemicellulose, and 15-30% of lignin, though the contents vary according to raw materials. Therefore, use of hemicellulose, which mainly contains the pentose xylose, but not only cellulose, which is a polymer of hexose, as a substrate should lead to effective ethanol production.

Xylose is reported to be the second abundant sugar in biomass next to glucose and it is an important object in bioethanol production to use pentose effectively.

Techniques for using xylose, even at a little amount, by imparting the ability to utilize xylose by genetic recombination, using microorganism that produces ethanol from xylose, or the like have been so far disclosed.

Patent Literature 1 discloses an invention involving converting xylose (C5) into xylulose by introducing a gene having the xylose transporter activity into a host cell to incorporate it in the pentose phosphate pathway of the glycolysis and use it for fermentation.

Patent Literature 2 discloses a technique for producing alcohol with yeast provided with an arabinose transporter. This involves incorporation of arabinose (C5) via arabitol and xylulose in the pentose phosphate pathway in the glycolysis to use it for fermentation, similar to the invention of Patent Literature 1.

Non-Patent Literature 1 discloses provision of xylose utilization ability by incorporating a xylose utilization gene derived from *Escherichia coli* in *Zymomonas*.

Non-Patent Literature 2 describes production of ethanol from xylose by yeast in the genus *Pichia*.

CITATION LIST

Patent Literature

Patent Literature 1:
Japanese Patent Laid-Open No. 2012-170422
Patent Literature 2:
U.S. Patent Application Publication No. 2013/189788

Non Patent Literature

Non Patent Literature 1:
Zhang, M., et al., Science, 1995. Vol. 267, pp. 240-243.
Non Patent Literature 2:
Bicho, P. A., et al., Appl. Environ. Microbiol., 1988, Vol. 54, pp. 50-54.

SUMMARY OF INVENTION

Technical Problem

However, the invention of Patent Literature 1 involves introducing a protein having the xylose transporter activity derived from *Candida guilliermondii* into *Saccharomyces cerevisiae* as a host. Accordingly, a foreign gene would be introduced.

The invention of Patent Literature 2 is also an invention involving introduction of a gene from a species different from the host, although the transporter gene is different.

The technique described in Non-Patent Literature 1 also involves introduction of a xylose utilization gene. The technical concept thereof is different from Patent Literature 1 and 2 described above, but they are similar in that a foreign gene is introduced.

Therefore, any of the invention described in Patent Literature 1 and 2 and Non-Patent Literature 1 requires adopting a containment measure to comply with "the Cartagena Protocol on Biosafety to the Convention on Biological Diversity" adopted in the United Nations. Accordingly, they require facilities for ensuring the biosafety and therefore it is disadvantageous in cost to produce ethanol using such yeasts.

Moreover, use of yeast in the genus *Pichia* by the technique described in Non-Patent Literature 2 does not result in a much higher efficiency of ethanol production because the low xylose availability in the wild-type *Pichia* yeast.

An object of the present invention is to obtain a fermentative yeast having a highly efficient ethanol production without introducing a foreign gene.

Solution to Problem

The present invention features a fermentative yeast that effectively produces ethanol from pentose and hexose and is deposited to NITE Patent Microorganisms Depositary (NITE Patent Microorganisms Depositary, National Institute of Technology and Evaluation (Independent Administrative Institution), #122, 2-5-8 Kazusakamatari, Kisarazu-shi, Chiba 292-0818, Japan) on Nov. 19, 2014 (accession date) under the accession number NITE BP-01964 (hereinafter, also referred to as strain BP-01964).

The wild-type *Meyerozyma guilliermondii* has a xylose utilization ability. However, it does not have sufficient ability to utilize xylose for the bioethanol production. The strain BP-01964 was obtained by the strain improvement of *Meyerozyma guilliermondii* and selection of yeasts that utilize pentose at a high efficiency. As a result, a yeast comprising ethanol productivity about twice as high as that of the parental strain was selected.

Moreover, the present invention features introduction of a self-cloned transaldolase, alcohol dehydrogenase, pyruvate decarboxylase, xylose reductase, xylitol dehydrogenase, transketolase, or formate dehydrogenase into the aforementioned *Meyerozyma guilliermondii* strain.

The introduction of an enzyme gene from *Meyerozyma guilliermondii* itself does not necessitate any containment measure to comply with the Cartagena Act. Therefore, conventional facilities can be used without needing special facilities for biosafety.

DESCRIPTION OF EMBODIMENTS

The ascomycete yeast *Meyerozyma guilliermondii* comprises the xylose utilization ability. A yeast of the accession number NITE BP-01964 was obtained using the strain N of *Meyerozyma guilliermondii* as the parent strain by the breeding involving selection of mutants with mutagenesis.

In general, mutagenesis involves use of irradiation of ultraviolet rays or radioactive rays, alkylating agents such as N-ethyl-N-nitrosourea (ENU) and ethyl methanesulfonate (EMS), base analogs such as BrdU, or nitroso compounds such as nitroamine or nitrosoguanidine. In the present invention, mutagenesis was carried out by irradiation of UV or addition of a chemical such as EMS.

Methods for obtaining yeast strains are described below.

Examples

1. Isolation of Yeast Strain

The parent strain of *Meyerozyma guilliermondii* was cultured with a sugar solution derived from rice straw. Rice straw from Kumagaya, Japan was immersed in an equal amount of a 25% ammonium solution at 80° C. for 3 hours and then ammonia was allowed to be evaporated. The pH of the treated biomass was adjusted to 4 with 10% NaOH and then *Acremonium* cellulase (manufactured by Meiji Seika Pharma Co., Ltd.) was added to conduct enzymatic saccharification at 50° C. for 72 hours. The solid-liquid separation of the produced slurry was conducted by filter-pressing to collect the liquid. Using this liquid (hereinafter, also referred to as clear liquid), habituation in culture was conducted with addition of a mutagen for 19 months and strains with improved fermentation performance were selected. The selection was based on the amount of ethanol after a certain time period. A strain with high fermentation performance was deposited to NITE Patent Microorganisms Depositary, National Institute of Technology and Evaluation (Independent Administrative Institution) under the accession number NITE BP-01964.

2. Properties of the Strain 2.1 Ethanol Production Ability

Figure 1:
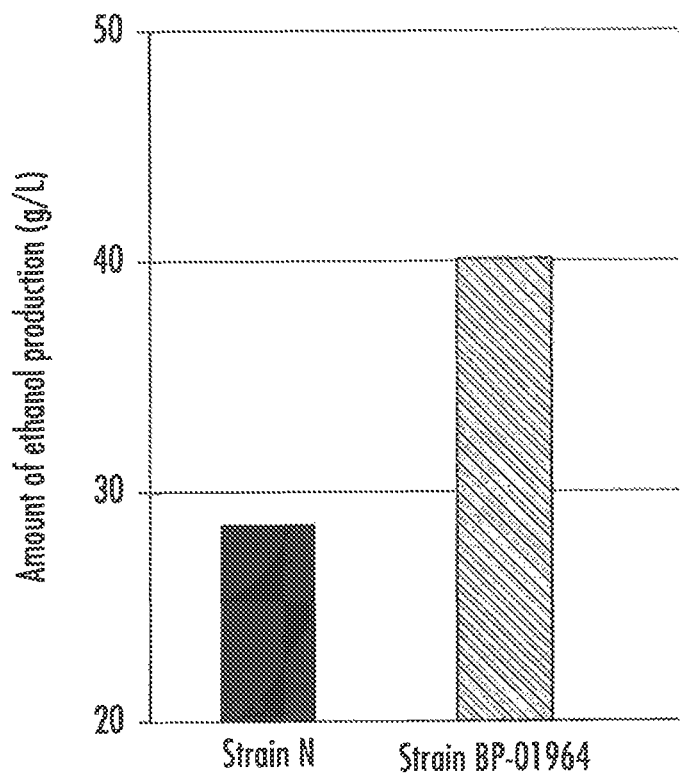
FIG. 1 illustrates the amounts of ethanol production in the strain BP-01964 and the parent strain (the strain N).

FIG. 1 illustrates the amount of ethanol production in the strain BP-01964 in comparison with that of the strain N, the parent strain. Corn stover was treated with dilute sulphuric acid and the resultant saccharified liquid whose pH was adjusted to 6 with an NaOH aqueous solution was used. A liquid culture of the strain was added so that the $OD_{600}$ of the medium became 2.0 and the resultant liquid culture was cultured at 30° C. for 96 hours. The amount of ethanol after the culturing is illustrated. Glucose in the saccharified solution was 63.2 g/L and xylose was 34.5 g/L. Ethanol was measured using GC-FID (manufactured by GL Sciences Inc.: GC390B).

As seen in FIG. 1, the obtained strain produces ethanol more than 2 times as much as the wild type does. Since the obtained strain has an improved ethanol production relative to the wild type strain, the obtained strain is considered to have an improved ability to utilize xylose, which is C5. Therefore, the glucose and xylose utilization abilities of the strain were examined.

Next, rice straw was treated with an ammonium aqueous solution in a similar way to the ammonia treatment described above and then *Acremonium* cellulase was added to conduct enzymatic saccharification at 50° C. for 72 hours. Fermentation was conducted using the produced slurry.

The slurry fermenter has a jacket structure and the temperature was regulated by the circulation of warm water through the jacket part. Air ports are provided at the bottom and fermentation was conducted with continuously providing a predetermined amount of filtered air through the air ports at the bottom with agitation with impellers coupled with a motor.

Figure 2:
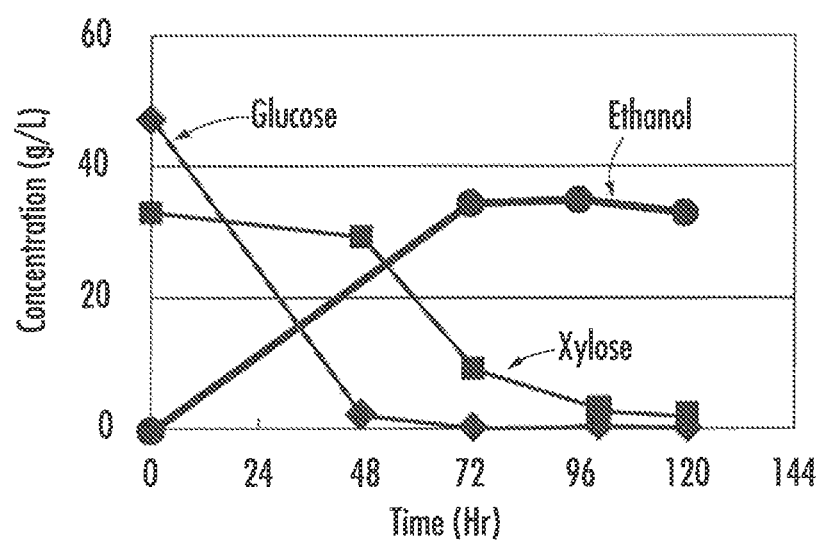
FIG. 2 illustrates glucose and xylose utilization abilities in slurry fermentation.

The change over time in amount of glucose, xylose, and ethanol contained in the slurry was analyzed. Glucose and xylose were measured by sampling and centrifuging the slurry and measuring the resultant supernatant by HPLC. Ethanol was measured using GC-FID (manufactured by GL Sciences Inc.: GC390B) as described above. The result is shown in FIG. 2.

Glucose, which is C6, is consumed earlier, but as glucose in the slurry decreases, xylose, which is C5, is consumed to produce ethanol. Since the obtained yeast comprises both C5 and C6 utilization abilities, it can produce ethanol efficiently. Therefore, it is a strain that is also useful in industrial production.

2.2 Slurry Fermentation Ability, Clear Liquid Fermentation Ability

A yeast that efficiently carries out fermentation both with slurry and with clear liquid in the bioethanol production is preferred. Therefore, the fermentation yields with slurry and with clear liquid were compared. The fermentation yield is calculated by the following equation.

Fermentation yield=amount of obtained ethanol (g/L)/amount of glucose+xylose contained in sugar solution at the onset of fermentation (g/L)/0.5114

Figure 3:
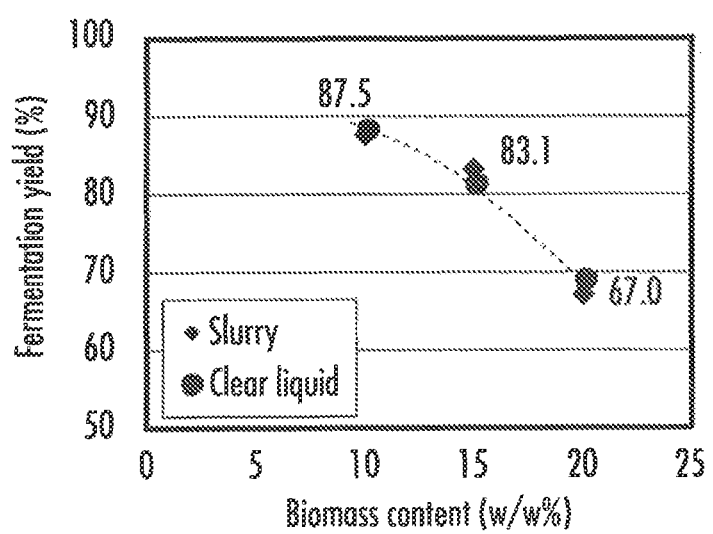
FIG. 3 illustrates yields of fermentation in slurry fermentation and in clear liquid fermentation.

As illustrated in FIG. 3, the obtained strain can exhibit equivalent performance both in slurry fermentation and in clear liquid fermentation.

2.3 Ethanol Production Ability with Corn Stover Sugar Liquid

Like rice straw, corn stover is biomass often used for bioethanol production. The obtained strain efficiently produces bioethanol with corn stover as well, although it is a strain isolated by conducting habituation with a clear liquid produced from rice straw.

Corn stover from Iowa, the United States, was immersed into 2 times volume of 3.7% by weight sulfuric acid aqueous solution and treated at 170° C. for 10 minutes. After transfer to normal temperature, pH of the solution was adjusted to pH 4 with a 4 M sodium hydroxide aqueous solution and an enzyme for biomass saccharification (such as *Acremonium* cellulase, manufactured by Meiji Seika Pharma Co., Ltd.) was added to conduct enzymatic saccharification at 50° C. for 72 hours. The solid-liquid separation of the produced slurry was conducted by centrifugation to collect the liquid (hereinafter, referred to as corn stover clear liquid).

Figure 4:
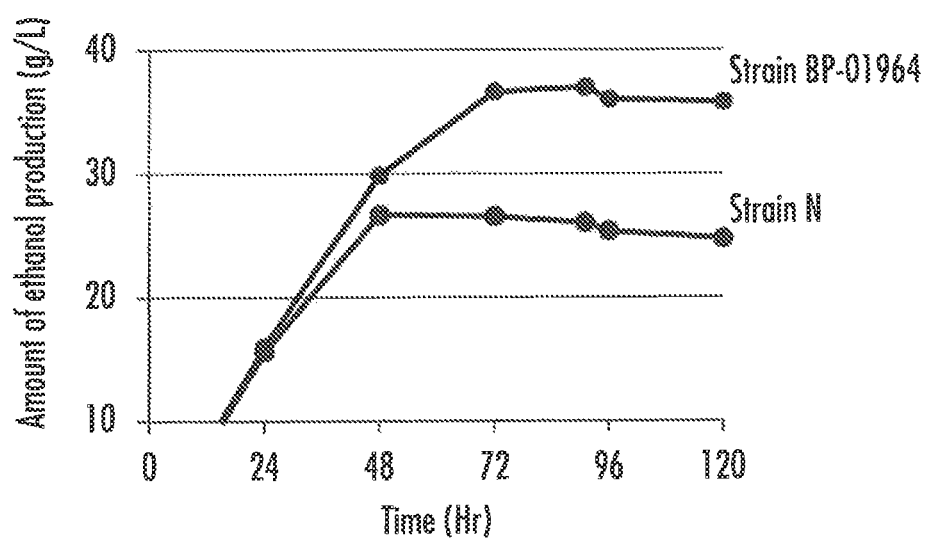
FIG. 4 illustrates the ethanol production ability of the strain BP-01964 with a corn stover clear liquid.

Fermentation with a corn stover clear liquid whose pH was adjusted to pH 6 with an NaOH aqueous solution was conducted with the obtained strain and the amount of ethanol production was measured over time. The result is shown in FIG. 4. While the ethanol production of the wild type (the strain N) reaches a plateau after 48 hours, the obtained strain continues producing ethanol until 72 hours later and can produce ethanol at a final yield that is about 1.5 times as high as that of the wild type.

Moreover, transaldolase, which is an enzyme in the pentose phosphate pathway, alcohol dehydrogenase, which is an enzyme that produces ethanol from acetaldehyde, or pyruvate decarboxylase, which produces acetaldehyde, which is a substrate of alcohol dehydrogenase from pyruvic acid, can be genetically introduced into the strain obtained in the present invention to further facilitate use of xylose.

For example, the following procedures can be adopted for the genetic introduction. Amplify the gene to be introduced and a terminator region thereof (hereinafter, referred to as gene+terminator region) by PCR. Amplify a promoter region to be used for the introduction. These should be both amplified by PCR from the chromosomes of the strain of *Meyerozyma guilliermondii* used in the present invention.

Clone the DNA fragments amplified by PCR into a commercially available vector for *Escherichia coli* by infusion in the order of promoter, gene+terminator region. Transform *Escherichia coli* with the cloned vector and amplify the vector. Obtain DNA fragments for homologous recombination by cutting out the promoter and gene+terminator region from the amplified vector with restriction enzymes or amplifying the promoter and gene+terminator region from the amplified vector by PCR Homologous recombination of the strain with the obtained DNA fragments was performed to obtain a desired strain. Electroporation was used for the homologous recombination. Genetic introduction in this manner allows introduction of multiple copies into the chromosomes and therefore enhancement of the activity of the introduced enzyme.

As a DNA fragment for the homologous recombination, for example, the promoter of xylose reductase, transaldolase+terminator may be preferably used because transaldolase is considered to work efficiently when using the promoter of xylose reductase that functions in the xylose utilization.

Specifically, the xylose reductase promoter is amplified with the following primers of SEQ ID NO: 1 and SEQ ID NO: 2 and the transaldolase gene and the terminator region were amplified with the following primers of SEQ ID NOs: 3 and 4.

```
SEQ ID NO: 1:
AAGGCTTGGGAACTTTCTTT

SEQ ID NO: 2:
AGCAATTGATGATTAATTTT

SEQ ID NO: 3:
ATGACCAATTCTCTTGAACA

SEQ ID NO: 4:
AAATTGTGCCGTGTCAAACT
```

Moreover, the promoter of GAPDH and alcohol dehydrogenase+terminator may be preferably used. Since the GAPDH is a strong promoter that functions in glycolysis, it is considered to be an efficient promoter for use as a promoter of alcohol dehydrogenase, which is an enzyme in glycolysis. Alcohol dehydrogenase produces $NAD^+$ when it is NADH-dependent as well as serves to convert acetaldehyde into ethanol. Therefore, it serves to enhance the effect of $NAD^+$-dependent xylitol dehydrogenase.

Specifically, the GAPDH promoter is amplified with the primers of the following SEQ ID NO: 5 and SEQ ID NO: 6 and the alcohol dehydrogenase gene and terminator region is amplified with the primers of the following SEQ ID NOs: 7 and 8.

```
SEQ ID NO: 5:
GTTCiTAGCGGAGGVTCAATT

SEQ ID NO: 6:
TGTATAATTTAAATGTGGGT

SEQ ID NO: 7:
ATGTCAATTCCAGAATCCAT

SEQ ID NO: 8:
CACCTTGGCTGGAAGTGCTG
```

Furthermore, besides transaldolase and alcohol dehydrogenase, enzymes such as pyruvate decarboxylase, xylose reductase, xylitol dehydrogenase, transketolase, and formate dehydrogenase may be cloned in the down stream of any of the aforementioned promoters and introduced into the obtained strain to confer resistance to organic acids such as acetic acid, aldehyde such as furfural, and the like, which are present when a sugar solution is produced.

Pyruvate decarboxylase, xylose reductase, xylitol dehydrogenase, transketolase, and formate dehydrogenase can be amplified with the following primers.

```
Pyruvate decarboxylase
SEQ ID NO: 9:
ATGACAGAAATTACTTTGGG

SEQ ID NO: 10:
ACAAACAAATGCTGAAAAC

Xylose reductase (XR)
SEQ ID NO: 11:
ATGTCTATTACTTTGAACTC

SEQ IN NO: 12:
CAC AAAAGTFGGAATCTTGT

Xylitol dehydrogenase (XDH)
SEQ ID: NO 13:
ATGACTCCCAACCCATCTTT

SEQ ID NO: 14:
CTCGGGACCATCTATAATAA

Transketolase (MK)
SEQ ID NO: 15:
ATGACCACCGACGACTACGA

SEQ ID NO: 16:
AACAGCTAGCAAGTCCTGA

Formate dehydrogenase (FDH)
SEQ ID NO: 17:
ATGAGTCCAGCAACAAAAGG

SEQ ID NO: 18:
ITTCATCITGTGTCTITCAC
```

Moreover, while the strains obtained by this method comprise an introduced gene, they belong to a category to be treated as a non-modified yeast under the Cartagena Act because it is self-cloned.

The strain BP-01964 has a xylose utilization ability enhanced by breeding in comparison with the wild type *Meyerozyma guilliermondii*, as described above, and is capable of effectively producing ethanol both from rice straw and from corn stover used as biomass.

The invention claimed is:

1. An ethanol-fermentative yeast, the ethanol-fermentative yeast being effective to produce ethanol from pentose and hexose and deposited to NITE Patent Microorganisms Depositary under the accession number NITE BP-01964 into which at least one gene selected from self-cloned pyruvate decarboxylase and formate dehydrogenase is introduced.

* * * * *

SEQUENCE LISTING

<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Meyerozyma guilliermondii

<400> SEQUENCE: 1
aaggcttggg aactttcttt                                              20

<210> SEQ ID NO 2
<211> LENGTH: 20
<212> TYPE: DNA
<213> ORGANISM: Artificial Sequence
<220> FEATURE:
<223> OTHER INFORMATION: Meyerozyma guilliermondii

<400> SEQUENCE: 2
agcaattgat gattaatttt                                              20

<210> SEQ ID NO 3
<211> LENGTH: 20
<212> TYPE: DNA
<213> ORGANISM: Artificial Sequence
<220> FEATURE:
<223> OTHER INFORMATION: Meyerozyma guilliermondii

<400> SEQUENCE: 3
atgaccaatt ctcttgaaca                                              20

<210> SEQ ID NO 4
<211> LENGTH: 20
<212> TYPE: DNA
<213> ORGANISM: Artificial Sequence
<220> FEATURE:
<223> OTHER INFORMATION: Meyerozyma guilliermondii

<400> SEQUENCE: 4
aaattgtgcc gtgtcaaact                                              20

<210> SEQ ID NO 5
<211> LENGTH: 20
<212> TYPE: DNA
<213> ORGANISM: Artificial Sequence
<220> FEATURE:
<223> OTHER INFORMATION: Meyerozyma guilliermondii

<400> SEQUENCE: 5
gttgtagcgg aggctcaatt                                              20

<210> SEQ ID NO 6
<211> LENGTH: 20
<212> TYPE: DNA
<213> ORGANISM: Artificial Sequence
<220> FEATURE:
<223> OTHER INFORMATION: Meyerozyma guilliermondii

<400> SEQUENCE: 6
tgtataattt aaatgtgggt                                              20

<210> SEQ ID NO 7
<211> LENGTH: 20
<212> TYPE: DNA
<213> ORGANISM: Artificial Sequence

```
<220> FEATURE:
<223> OTHER INFORMATION: Meyerozyma guilliermondii

<400> SEQUENCE: 7
atgtcaattc cagaatccat                                                   20

<210> SEQ ID NO 8
<211> LENGTH: 20
<212> TYPE: DNA
<213> ORGANISM: Artificial Sequence
<220> FEATURE:
<223> OTHER INFORMATION: Meyerozyma guilliermondii

<400> SEQUENCE: 8
caccttggct ggaagtgctg                                                   20

<210> SEQ ID NO 9
<211> LENGTH: 20
<212> TYPE: DNA
<213> ORGANISM: Artificial Sequence
<220> FEATURE:
<223> OTHER INFORMATION: Meyerozyma guilliermondii

<400> SEQUENCE: 9
atgacagaaa ttactttggg                                                   20

<210> SEQ ID NO 10
<211> LENGTH: 19
<212> TYPE: DNA
<213> ORGANISM: Artificial Sequence
<220> FEATURE:
<223> OTHER INFORMATION: Meyerozyma guilliermondii

<400> SEQUENCE: 10
acaaacaaat gctgaaaac                                                    19

<210> SEQ ID NO 11
<211> LENGTH: 20
<212> TYPE: DNA
<213> ORGANISM: Artificial Sequence
<220> FEATURE:
<223> OTHER INFORMATION: Meyerozyma guilliermondii

<400> SEQUENCE: 11
atgtctatta ctttgaactc                                                   20

<210> SEQ ID NO 12
<211> LENGTH: 20
<212> TYPE: DNA
<213> ORGANISM: Artificial Sequence
<220> FEATURE:
<223> OTHER INFORMATION: Meyerozyma guilliermondii

<400> SEQUENCE: 12
cacaaaagtt ggaatcttgt                                                   20

<210> SEQ ID NO 13
<211> LENGTH: 20
<212> TYPE: DNA
<213> ORGANISM: Artificial Sequence
<220> FEATURE:
<223> OTHER INFORMATION: Meyerozyma guilliermondii

<400> SEQUENCE: 13
atgactccca acccatcttt                                                   20
```

<210> SEQ ID NO 14
<211> LENGTH: 20
<212> TYPE: DNA
<213> ORGANISM: Artificial Sequence
<220> FEATURE:
<223> OTHER INFORMATION: Meyerozyma guilliermondii

<400> SEQUENCE: 14
ctcgggacca tctataataa                                        20

<210> SEQ ID NO 15
<211> LENGTH: 20
<212> TYPE: DNA
<213> ORGANISM: Artificial Sequence
<220> FEATURE:
<223> OTHER INFORMATION: Meyerozyma guilliermondii

<400> SEQUENCE: 15
atgaccaccg acgactacga                                        20

<210> SEQ ID NO 16
<211> LENGTH: 19
<212> TYPE: DNA
<213> ORGANISM: Artificial Sequence
<220> FEATURE:
<223> OTHER INFORMATION: Meyerozyma guilliermondii

<400> SEQUENCE: 16
aacagctagc aagtcctga                                         19

<210> SEQ ID NO 17
<211> LENGTH: 20
<212> TYPE: DNA
<213> ORGANISM: Artificial Sequence
<220> FEATURE:
<223> OTHER INFORMATION: Meyerozyma guilliermondii

<400> SEQUENCE: 17
atgagtccag caacaaaagg                                        20

<210> SEQ ID NO 18
<211> LENGTH: 20
<212> TYPE: DNA
<213> ORGANISM: Artificial Sequence
<220> FEATURE:
<223> OTHER INFORMATION: Meyerozyma guilliermondii

<400> SEQUENCE: 18
tttcatcttg tgtctttcac                                        20